United States Patent [19]
Kohayakawa

[11] Patent Number: 5,713,047
[45] Date of Patent: Jan. 27, 1998

[54] EYE FUNDUS PHOTOGRAPHING APPARATUS

[75] Inventor: Yoshimi Kohayakawa, Yokohama, Japan

[73] Assignee: Canon Kabushiki Kaisha, Tokyo, Japan

[21] Appl. No.: 352,443

[22] Filed: Dec. 9, 1994

Related U.S. Application Data

[63] Continuation of Ser. No. 70,238, Jun. 2, 1993, abandoned.

[30] Foreign Application Priority Data

Jun. 8, 1992 [JP] Japan ................................. 4-173826
Aug. 25, 1992 [JP] Japan ................................. 4-250693

[51] Int. Cl.$^6$ ................................. G03B 29/00; A61B 3/14
[52] U.S. Cl. ................................. 396/18; 351/206
[58] Field of Search ................................. 351/206, 207; 354/62; 396/14, 18

[56] References Cited

U.S. PATENT DOCUMENTS

| | | | |
|---|---|---|---|
| 4,322,137 | 3/1982 | Nohda | 351/7 |
| 4,449,798 | 5/1984 | Nohda | 351/207 |
| 4,558,932 | 12/1985 | Nunokawa | 351/206 |
| 4,679,919 | 7/1987 | Itoh et al. | 351/206 |
| 4,704,018 | 11/1987 | Takhashi | 351/206 |
| 4,834,526 | 5/1989 | Nunokawa | 351/206 |
| 4,838,680 | 6/1989 | Nowokawa | 354/62 |
| 4,856,890 | 8/1989 | Itoh et al. | 351/206 |
| 5,202,708 | 4/1993 | Sasaki et al. | 351/206 |
| 5,214,454 | 5/1993 | Sano | 351/206 |
| 5,249,004 | 9/1993 | Kitajima | 351/206 |
| 5,255,026 | 10/1993 | Arai et al. | 351/206 |
| 5,302,988 | 4/1994 | Nanjo | 354/62 |
| 5,315,329 | 5/1994 | McAdams | 351/206 |

FOREIGN PATENT DOCUMENTS 615729  2/1986  Japan.

*Primary Examiner*—Safet Metjahic
*Assistant Examiner*—Nicholas J. Tuccillo
*Attorney, Agent, or Firm*—Fitzpatrick, Cella, Harper & Scinto

[57] ABSTRACT

An eye fundus photographing apparatus has an illumination system for illuminating an eye fundus under test by an illumination light beam, a photographing system for photographing the eye fundus under test by a photographing light beam from the eye fundus under test illuminated by the illumination system, and a light shielding member arranged at a vicinity of the illumination diaphragm or the photographing diaphragm or at a vicinity of a conjugate position of the diaphragms, wherein it is an object of the present invention to provide an eye fundus photographing apparatus which enables eye fundus photographing to be in a good condition to an eye under test having a small pupil diameter.

22 Claims, 15 Drawing Sheets

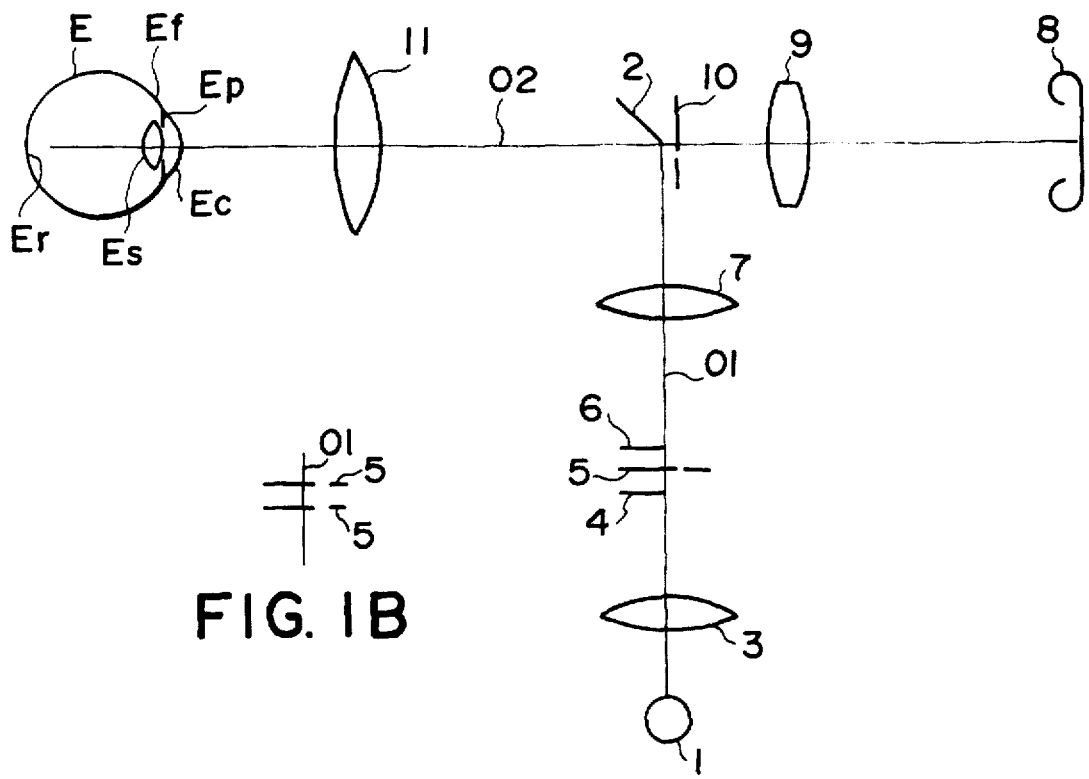
FIG. 1B
FIG. 1A
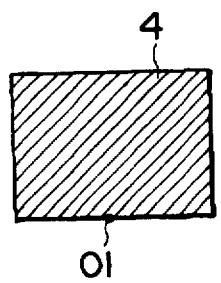
FIG. 2
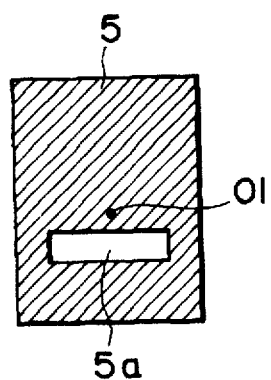
FIG. 3

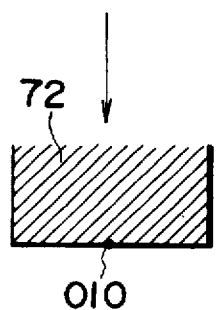
F I G. 24
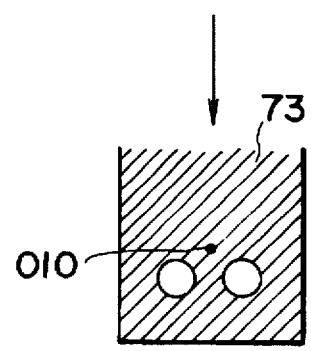
F I G. 25
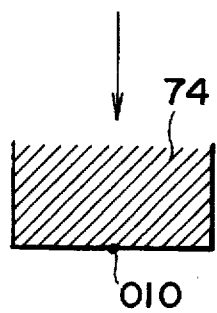
F I G. 26
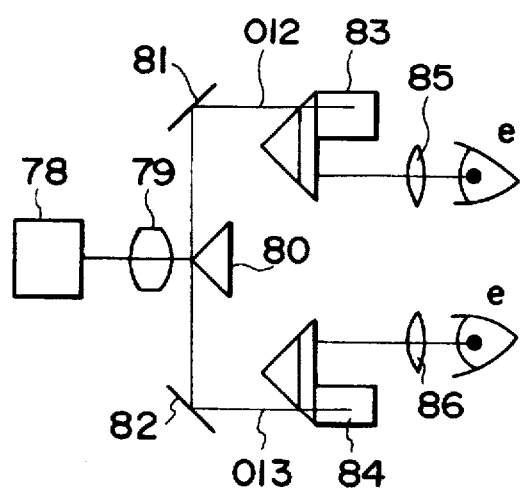
F I G. 27

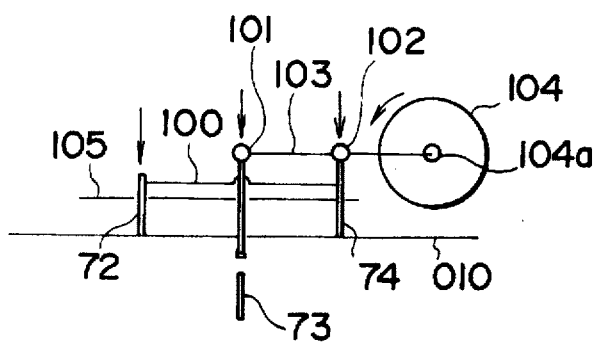
F I G. 31
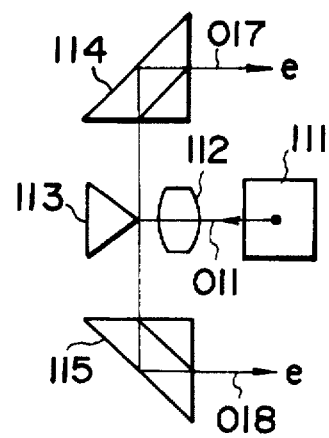
F I G. 32
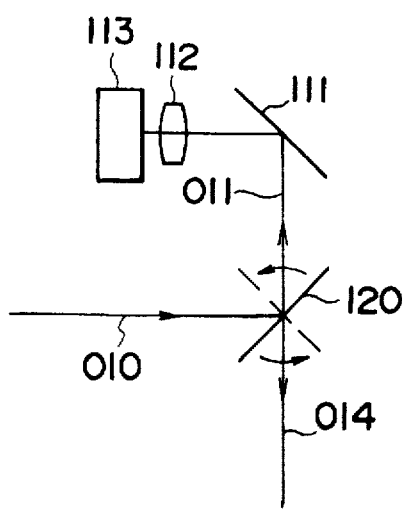
F I G. 33

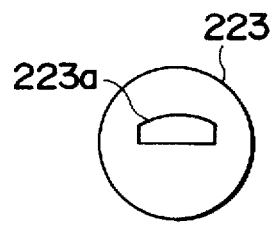 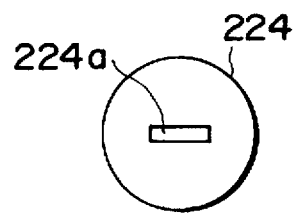
FIG. 36A  FIG. 36B
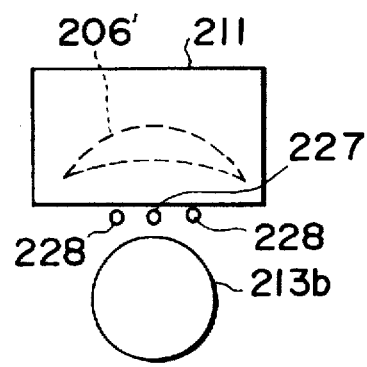
FIG. 37
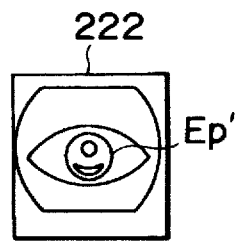
FIG. 38

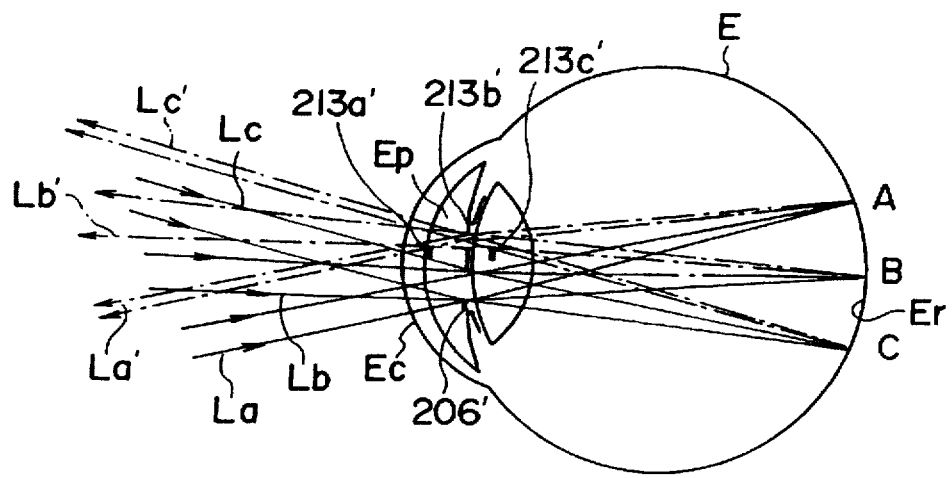
FIG. 39
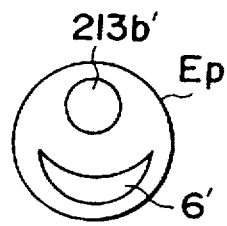
FIG. 40
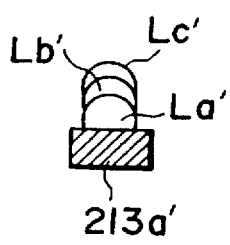    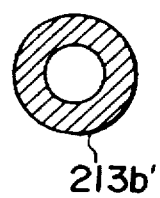    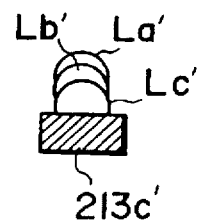
FIG.41A        FIG.41B        FIG.41C

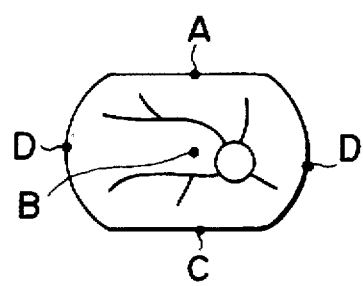
F I G. 42
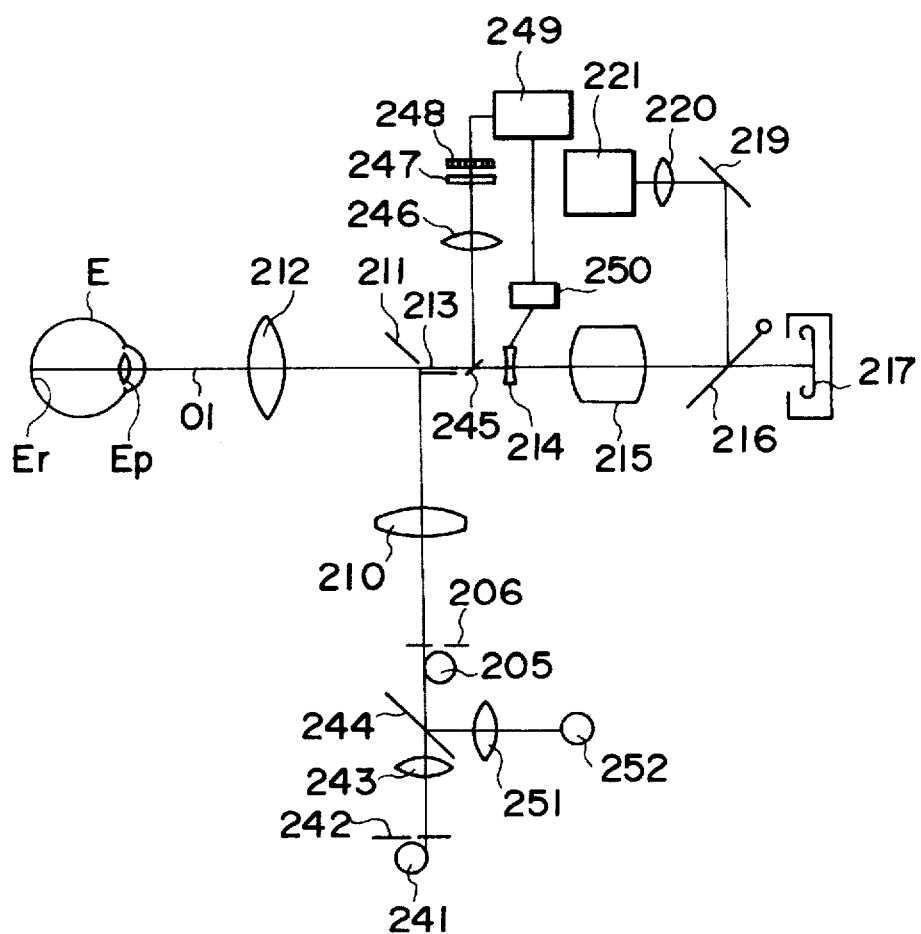
F I G. 43

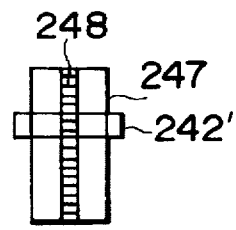
F I G. 44
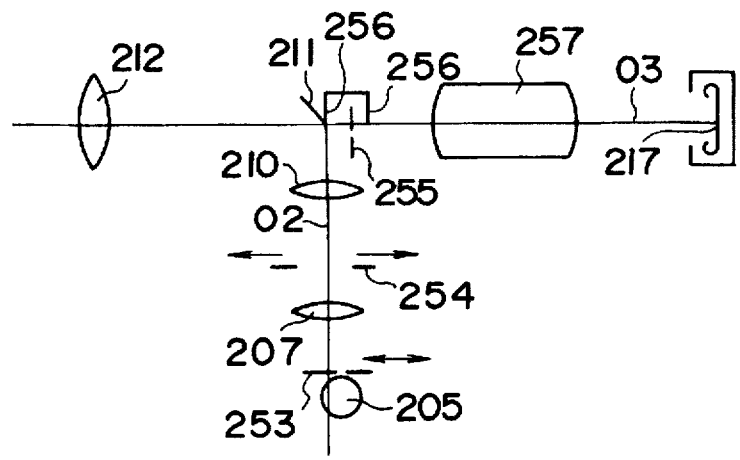
F I G. 45
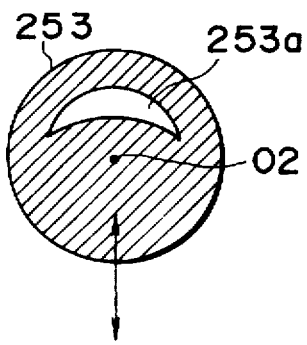
F I G. 46
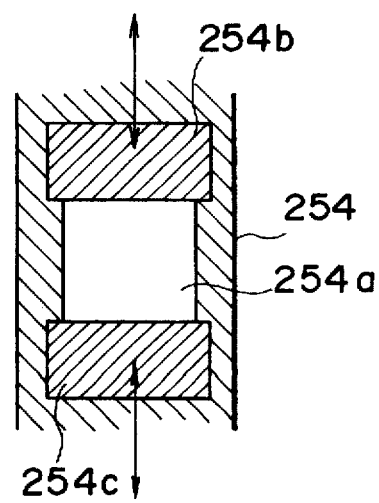
F I G. 47

EYE FUNDUS PHOTOGRAPHING APPARATUS

This application is a continuation of application Ser. No. 08/070,238 filed Jun. 2, 1993, now abandoned.

BACKGROUND OF THE INVENTION

1. Field of the Invention

The present invention relates to an eye fundus photographing apparatus used in an ophthalmic clinic.

2. Related Background Art

In a prior art eye fundus photographing camera, an eye fundus is illuminated from a periphery of a pupil by using an apertured mirror and a ring slit, and a light beam reflected by the eye fundus is taken out of the center of the pupil to take a photograph thereof.

Japanese Laid-Open Patent Application No. 61-5729 discloses a method for photographing the eye fundus while aligning a view axis to a center of an optical axis by using a ring slit located at a position which is conjugate with the pupil and light shielding members for the optical axis light beam located in front and back thereof.

However, in the former prior art apparatus, a large scattering pupil is required when a view angle is wide or a stereoscopic photographing is to be effected and if the scattering pupil is small, the image quality is degraded. Further, in a peripheral photographing or the photographing with an insufficient scattering pupil, it is likely that the exposure is short.

In the latter prior art apparatus, since the eye fundus of the eye to be tested is illuminated through the ring slit, the illumination becomes non-uniform when the eye to be tested has a small pupil.

SUMMARY OF THE INVENTION

It is an object of the present invention to provide an eye fundus photographing apparatus which enables eye fundus photographing to be in a good condition to an eye under test having a small pupil diameter.

Other objects of the present invention will be apparent from the description of the preferred embodiments to be described hereinafter.

BRIEF DESCRIPTION OF THE DRAWINGS

FIG. 1A shows a construction of a first embodiment.

FIG. 1B illustrates a variation of illumination diaphragm portion.

FIG. 2 shows a front view of a light shielding member,

FIG. 3 shows a front view of an illumination diaphragm,

FIG. 24 shows a front view of a light shielding member, FIG. 25 shows a front view of a photographing diaphragm, FIG. 26 shows a front view of a light shielding member, FIG. 27 shows a construction of an observation optical system.

FIG. 31 shows a construction of drive means for a light shielding member and a photographing diaphragm, FIG. 32 shows a construction of a modification, FIG. 33 shows a construction of a modification, FIGS. 36A and 36B show front views of a diaphragm, FIG. 37 shows a front view of a half-mirror, FIG. 38 shows a mark on a television monitor, FIG. 39 shows an optical path in an eye, FIG. 40 shows a front view of a pupil, FIGS. 41A, 41B and 41C show sectional views of light beams on a pupil plane and a diaphragm plane, FIG. 42 illustrates an eye fundus, FIG. 43 shows a construction of a seventh embodiment, FIG. 44 illustrates a slit light beam on a CCD, FIG. 45 shows a construction of an eighth embodiment, FIG. 46 shows a front view of an illumination diaphragm, FIG. 47 shows a front view of a view field diaphragm.

DETAILED DESCRIPTION OF THE PREFERRED EMBODIMENTS

An eye fundus camera in an embodiment described below comprises an illumination diaphragm located in a conjugate relation on one side of a pupil of an eye under test, a photographing diaphragm located in a conjugate relation on the other side, and a light shielding member located in a conjugate relation to a crossing area of an illumination and photographing light beams in a vicinity of the illumination diaphragm or the photographing diaphragm.

In the eye fundus camera of the present embodiment, light paths of the eye fundus illumination light beam and the eye fundus reflected light beam are separated at a front portion of the eye by a light shielding member, and the eye fundus is illuminated from one side of the pupil and the reflected light beam from the eye fundus is taken out of the other side for photographing.

Figure 4:
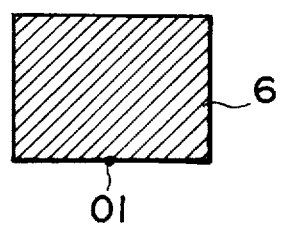
FIG. 4 shows a front view of a light shielding member.

FIG. 1 shows a construction of the first embodiment, arranged on an optical axis 01 extending from an eye fundus illumination light source 1 to a half-mirror 2 (hereinafter "half-mirror" is defined as a mirror located at such position where a total reflection mirror is arranged against an optical path as shown in FIG. 1) are a lens 3, a light shielding member 4 shown in FIG. 2, an illumination diaphragm 5 having a rectangular aperture 5a shown in FIG. 3, a light shielding member 6 shown in FIG. 4 and a lens 7, and arranged on an optical axis 02 extending from a film 8 to an eye E under test are a lens 9, a photographing diaphragm 10, the half-mirror 2 and an objective lens 11. The illumination diaphragm 5, the light shielding member 4 and the light shielding member 6 are arranged in conjugate relations with a pupil Ep of the eye under test, a cornea Ec and a rear plane of a crystalline lens Es, respectively, and a crosspoint of the optical axes 01 and 02 is substantially conjugate with the pupil Ep.

The diaphragm 5 and members 4, 6 may be replaced by two diaphragms 5 which are arranged at front and rear positions of the conjugate position of the pupil Ep, respectively, as shown in FIG. 1B.

A light beam from the eye fundus illumination light source 1 passes through the lens 3, the light shielding member 4, the illumination diaphragm 5, the light shielding member 6 and the lens 7, is reflected by the half-mirror 2 and illuminates the eye fundus Er of the eye E under test through the objective lens 11. The reflected light from the eye fundus Er passes through the objective lens 11, the half-mirror 2, the photographing diaphragm 10 and the lens 9 and is focused on the film 8 as an eye fundus image.

Figure 5:
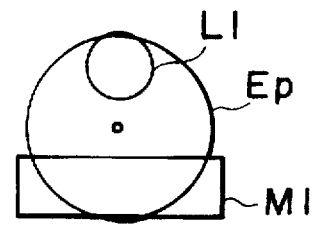
FIG. 5 illustrates a relation between an illumination light beam in a pupil and a photographing light beam.

FIG. 5 shows a relation between the illumination light beam M1 applied to the pupil Ep and the photographing light beam L1 taken out of the pupil Ep on the pupil Ep. As seen in FIG. 5, the area of the pupil corresponding to the position of the aperture of the diaphragm 5 and the area of the pupil corresponding to the aperture of the diaphragm 10, which are different, are spaced from each other in one direction and are not spaced from each other in a direction perpendicular to the one direction. The shape of the illumination light beam M1 depends on the shape of the aperture 5a of the illumination diaphragm 5 and the shape of the photographing light beam L1 depends on the shape of the aperture 10a of the photographing diaphragm 10.

Figure 6:
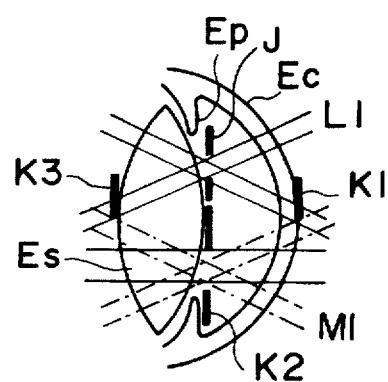
FIG. 6 shows a sectional view of a light beam in a front portion of the eye.

FIG. 6 shows a sectional view of a light beam in the front portion of the eye Ef. A chain line shows the illumination light beam M1, a solid line shows the photographing light beam L1 and thick lines K1 shows the image of the light shielding member 4, K2 shows the image of the illumination diaphragm 5 and K3 shows the image of the image shielding member 6. J shows the image of the photographing diaphragm 10.

A portion of the light beam from the eye fundus illumination light source 1 which illuminates the upper portion of the eye fundus Er is partially shielded by the light shielding member 6, and a portion which illuminates the lower portion of the eye fundus Er is partially shielded by the light shielding member 4 and the illumination light beam M1 and the photographing light beam L1 are separated without overlapping in the front portion of the eye Ef, between the cornea and the crystalline lens as shown in FIG. 6. As a result, the introduction of the scattered light by the cornea Ec and the crystalline lens Es of the eye E under test into the photographing light beam is prevented, and an eye fundus image of a high contrast can be attained. As shown in FIG. 6, it is most preferable that the conjugate positions K1 and K3 of the light shielding members 4 and 6 are on the cornea and the rear plane of the crystalline lens Es, respectively, or they may be in the vicinity thereof.

Figure 7:
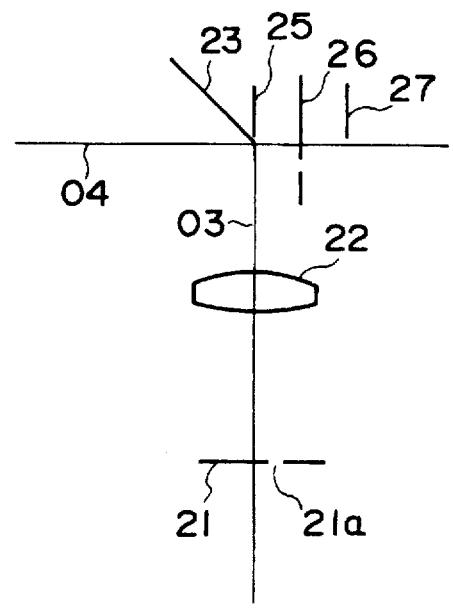
FIG. 7 shows a construction of a second embodiment.
Figure 8:
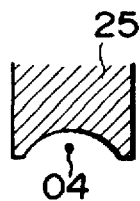
FIG. 8 shows a front view of a light shielding member.
Figure 9:
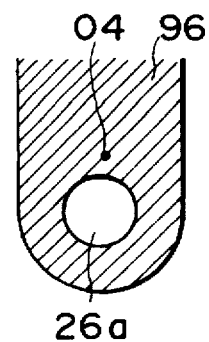
FIG. 9 shows a front view of a photographing diaphragm.
Figure 10:
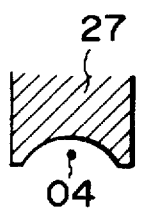
FIG. 10 shows a front view of a light shielding member, FIG. 11 illustrate a relation between an illumination light beam in a pupil and a photographing light beam.

FIG. 7 shows a portion of construction of a second embodiment. Arranged on an optical axis 03 are an illumination diaphragm 21 having a crescent-shaped aperture 21a, a lens 22 and a half-mirror 23, and arranged on an optical axis 04 are a light shielding member 25 shown in FIG. 8, a photographing diaphragm 26 having an aperture 26a shown in FIG. 9 and a light shielding member 27 shown in FIG. 10. The illumination diaphragm 21 and the photographing diaphragm 26 are in conjugate relation with the pupil Ep, and the light shielding members 25 and 27 are in conjugate relation with the front portion of the eye.

Figure 11:
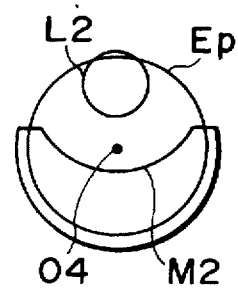

The effects of the present embodiment are the same as those of the first embodiment. A portion of the light beam reflected from eye fundus is shielded by the light shielding members 25 and 27, and the crescent-shaped illumination light beam M2 projected to the pupil shown in FIG. 11 and the circular photographing light beam L2 taken out of the pupil Ep are separated at the front portion of the eye.

When the aperture 21a of the illumination diaphragm 21 has a crescent shape, and if the light shielding members 25 and 27 in the photographing optical system also have analog shapes, then the light shield on the other side of the pupil Ep to which the illumination light beam M2 is projected becomes unnecessary. The light shielding members 4 and 6 provided in the illumination optical path in the first embodiment and the light shielding members 25 and 27 provided in the photographing optical path in the second embodiment may be used in combination. Where two photographing diaphragms are used, stereoscopic photographing can be attained.

The eye fundus camera described below comprises an apertured diaphragm located in conjugate relation with the pupil of the illumination system and light shielding members located on the optical axis in front and behind the apertured diaphragm for partially and substantially symmetrically shielding the light on the side of the optical axis of the oblique cross-section light beam passing through the optical axis, and has the apertured diaphragm and the light shielding members to separate the illumination light beam and the photographing light beam in the front portion of the eye.

The eye fundus camera partially and symmetrically shields the oblique cross-section light beam passing through the optical axis by the light shielding members located in the illumination optical path to separate the illumination light beam and the photographing light beam in the front portion of the eye.

Figure 12:
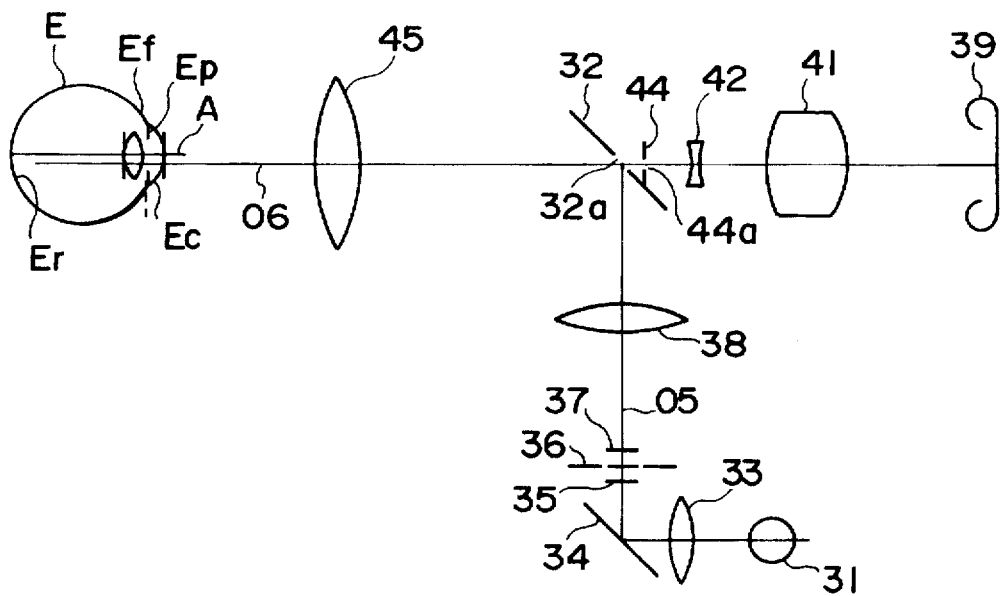
FIG. 12 shows a construction of a third embodiment.
Figure 13:
FIG. 13 shows a front view of a light shielding member.
Figure 14:
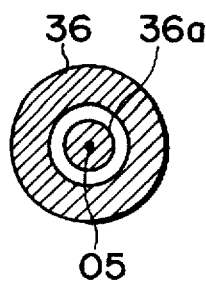
FIG. 14 shows a front view of a ring slit.
Figure 15:
FIG. 15 shows a front view of a light shielding member.

FIG. 12 shows a construction of a third embodiment. Arranged on an optical axis 05 extending from a light source 31 to an apertured mirror 32 are a condenser lens 33, a mirror 34, a light shielding member 35 shown in FIG. 13, a ring slit 36 having a ring-shaped aperture 36a shown in FIG. 14, a light shielding member 37 shown in FIG. 15, and a lens 38 to form an illumination optical system, and arranged on an optical axis 06 extending from a film 39 to an eye E under test are a lens 41, a focusing lens 42, a photographing diaphragm 44, an apertured mirror 32 and an objective lens 45 to form a photographing optical system.

A light beam from the light source 31 passes through the condenser lens 33, the mirror 34, the light shielding member 35, the ring slit 36, the light shielding member 37 and the lens 38, is reflected by the apertured mirror 32, and passes through the objective lens 45 to illuminate the eye fundus Er. The eye fundus reflected light beam is returned to the same optical axis 06 and passes through the objective lens 45, the aperture 32a of the apertured mirror 32, the photographing diaphragm 44, the focusing lens 42 and the lens 41, and is projected onto the film 39 as the eye fundus image through the lens 41.

Figure 16:
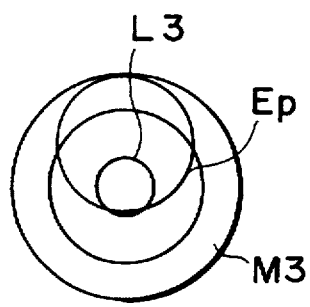
FIG. 16 illustrates a relation between an illumination light beam and a photographing light beam in a pupil.

As shown in FIG. 16, the illumination light beam M3 by the aperture 36a of the ring slit 36 is projected onto the eye fundus Er through the pupil Ep and the photographing light beam L3 is taken out of the aperture 44a of the photographing diaphragm 44.

Figure 17:
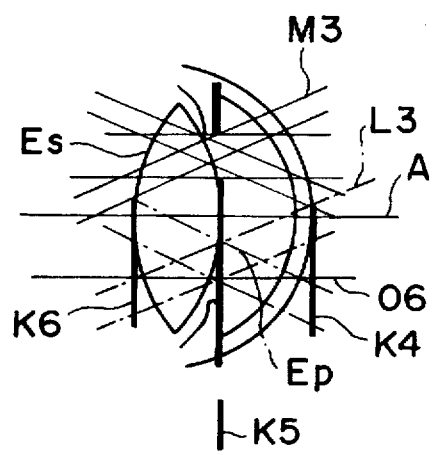
FIG. 17 shows a sectional view of a light beam in an eye fundus.

FIG. 17 shows a sectional view of a light beam in the front portion of the eye Ef. The illumination light beam M3 shown by a solid line is incident from the top of the pupil Ep and the photographing light beam L3 shown by a chain line which is the eye fundus reflected light beam outgoes from the bottom of the pupil Ep. The optical axis 06 is eccentric to a viewing axis A. A thick solid line shows conjugate positions of the light shielding members 35 and 37 and the ring slit 36 in the front portion of the eye Ef. The conjugate position K4 of the light shielding member 35 is located at the cornea Ec, the conjugate position K5 of the ring slit 36 is located at the pupil Ep, and the conjugate position K6 of the light shielding member 37 is located on the rear plane of the crystalline lens Es. Of the illumination light beam M3, a light beam inclined to the optical axis for illuminating the top of the eye fundus Er is shielded by the light shielding member 35, and a light beam for illuminating the bottom of the eye fundus Er is partially shielded by the light shielding member 37 on the side of the optical axis 06 equally to the light shielding by the light shielding member 35 so that the light beam passing through the center of the optical axis 06 is not blocked. As a result, the illumination light beam M3 and the photographing light beam L3 are separated at the front portion of the eye Ef without a crossing area and the light shielding is attained equally. Thus, an image without ununiformity in brightness and with a high contrast is attained.

Even if any portion of the illumination light beam M3 is projected from the pupil Ep to the eye fundus Er, it is separated from the photographing light beam L3 at the front portion of the eye Ef by the light shielding members 35 and 37 so that the entire area of the eye fundus Er is illuminated in a good condition. As shown in FIG. 16, where the pupil diameter is smaller than the ring-shaped illumination light beam M3, the photographing is effected by making the optical axis 06 eccentric to the sight axis A as shown in FIG. 12, and if the pupil Ep is sufficiently large, the photographing is effected without eccentricity.

It is most preferable that the light shielding members 35 and 37 are arranged such that the conjugate positions K4 and K5 shown in FIG. 17 are located at the cornea Ec and the rear plane of the crystalline lens Es, respectively.

In an eye fundus camera having a variable magnification function, the ring slit and the light shielding members of the prior art apparatus and the light shielding members 35 and 37 and the ring slit 36 of the present embodiment may be selectively used in accordance with the circumstance. The present embodiment is particularly applicable to a narrow angle telescoping photographing and whenever an eccentricity is one sided or the center of the image is not darkened. In photographing the periphery of the eye fundus, the eccentric photographing is preferable because an affect of the aberration of the eye optical system can be reduced.

In an eye fundus camera described below, a photographing diaphragm is provided in conjugate relation with the center of the pupil of the eye under test and a cylindrical lens is provided in the vicinity of the conjugate position of the photographing diaphragm.

The present eye fundus camera corrects the aberration of the eye optical system in the eccentric photographing by the cylindrical lens provided in the photographing optical system.

Figure 18:
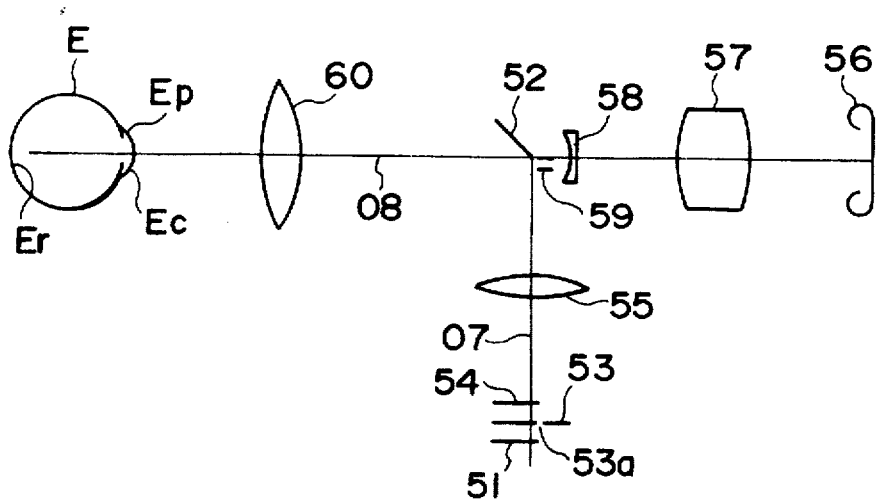
FIG. 18 shows a construction of a fourth embodiment.
Figure 19:
FIG. 19 shows a front view of a light shielding member.
Figure 20:
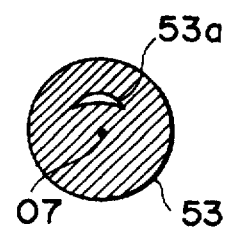
FIG. 20 shows a front view of an illumination diaphragm.
Figure 21:
FIG. 21 shows a front view of a light shielding member.

FIG. 18 shows a construction of a fourth embodiment. An illumination light source is not shown. Arranged on an optical axis 07 extending from a light shielding member 51 shown in FIG. 19 to a half-mirror 52 are an illumination diaphragm 53 having a crescent-shaped aperture 53a shown in FIG. 20, a light shielding member 54 shown in FIG. 21 and a relay lens 55. Arranged on an optical axis 08 extending from a film 56 to the eye E under test are a lens 57, a cylindrical lens 58, a photographing diaphragm 59 which is eccentric to the optical axis 08, a half-mirror 52 and an objective lens 60. As shown in FIGS. 18-20, the light shielding members 51 and 54 and the illumination diaphragm 53 are eccentric to the optical axis 08, and the photographing diaphragm 59 and the illumination diaphragm 53 are located in conjugate relation with the pupil of the eye under test.

A light beam from the light source, not shown, on the optical axis 07 passes through the light shielding member 51, the illumination diaphragm 53, the light shielding member 54, the condenser lens 55, the half-mirror 52 and the objective lens 60 and is projected to the eye fundus Er, and the eye fundus reflected light beam is returned through the same optical path, passes through the objective lens 60, the half-mirror 52, the photographing diaphragm 59, the cylindrical lens 58 and the lens 57, and is projected onto the film 56 as the eye fundus image.

Figure 22:
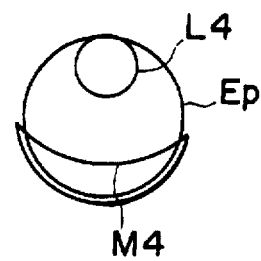
FIG. 22 illustrates a relation between an illumination light beam and a photographing light beam in pupil.

The effects of the present embodiment are same as those of the previous embodiments. Depending on the position of the light shielding members 51 and 54 shown in FIGS. 19 and 21 relative to the optical axis 07, the light beam from the aperture 53a of the illumination diaphragm 53 is partially shielded in the side of the optical axis 07 of the oblique light beam so that the illumination light beam is separated from photographing light beam in the front portion of the eye. As shown in FIG. 22, since the illumination diaphragm 53 and the photographing light beam 59 are eccentric to the optical axes 07 and 08, respectively, in the pupil Ep, the illumination light beam M4 and the photographing light beam L4 are also eccentric to the pupil Ep.

The cylindrical lens 58 has a refractive power in a plane of the drawing to correct an astigmatism created by the cornea Ec of the eye E under test. The cylindrical lens 58 may be located at an other conjugate position with pupil Ep in the photographing optical system. It may be eccentric to the optical axis 08 and aligned to the photographing diaphragm 59.

One of the embodiments described below is particularly effective to a non-midriatic pupil eye fundus camera for photographing a central portion of the eye fundus. Where a relation between the visual axis and the optical axis 08 is always constant, the aberration created in the eye optical system by the eccentric photographing can be corrected by the photographing optical system.

One of the eye fundus cameras described below comprises a reflection member for normally reflecting a light beam transmitted through an objective lens and a photographing optical system, a split reflection member for splitting a light beam reflected by the reflection member at the conjugate position with the pupil or in the vicinity thereof, to horizontally left and right optical paths and eye fundus image recording media provided on the respective optical paths split by the split reflection member.

One of the eye fundus cameras photographs the eye fundus reflected images split to the left and the right on the respective eye fundus image recording media to produce a set of stereoscopic photographs. An eye fundus camera described below comprises a reflection member for reflecting a horizontal optical path from the eye under test to a vertical optical path and directing it to observation means, and optical path switching means for rotating the reflection member by 90 degrees in photographing mode to direct the eye fundus reflected light beam to the photographing means.

One of the eye fundus cameras rotates the eye fundus reflected light beam to the reflection member to direct it to the observation means in the observation mode and to the photographing means in the photographing mode.

One of the eye fundus cameras described below illuminates the pupil from one side thereof and observes and photographs the pupil from the other side. The photographing diaphragm and the light shielding members in the vicinity thereof and integrally assembled and they are linked according to a variable magnification mechanism.

One of the present eye fundus cameras, the illumination light beam and the photographing light beam are separated in the pupil even in the variable magnification photographing mode by integrally driving the light shielding members and the photographing diaphragm.

One of eye fundus cameras described below comprises a light beam split member for splitting the illumination optical system and the photographing optical system to the conjugate positions with the pupil with respect to the objective lens, a first reflection member for vertically reflecting the light beam from the optical axis of the objective lens, a second reflection member for reflecting the light beam reflected by the first reflection member substantially parallelly to the optical axis of the objective lens, a split reflection member for reflecting and splitting the light beam reflected by the second reflection member to left and right optical paths at the conjugate position with the pupil or in the vicinity thereof, and a third reflection member for reflecting the left and right optical paths to an operator.

One of the present eye fundus cameras, the eye fundus reflected light beams reflected and split into two parts by the reflection members are directed to the eye under test and binocularly observed.

Figure 23:
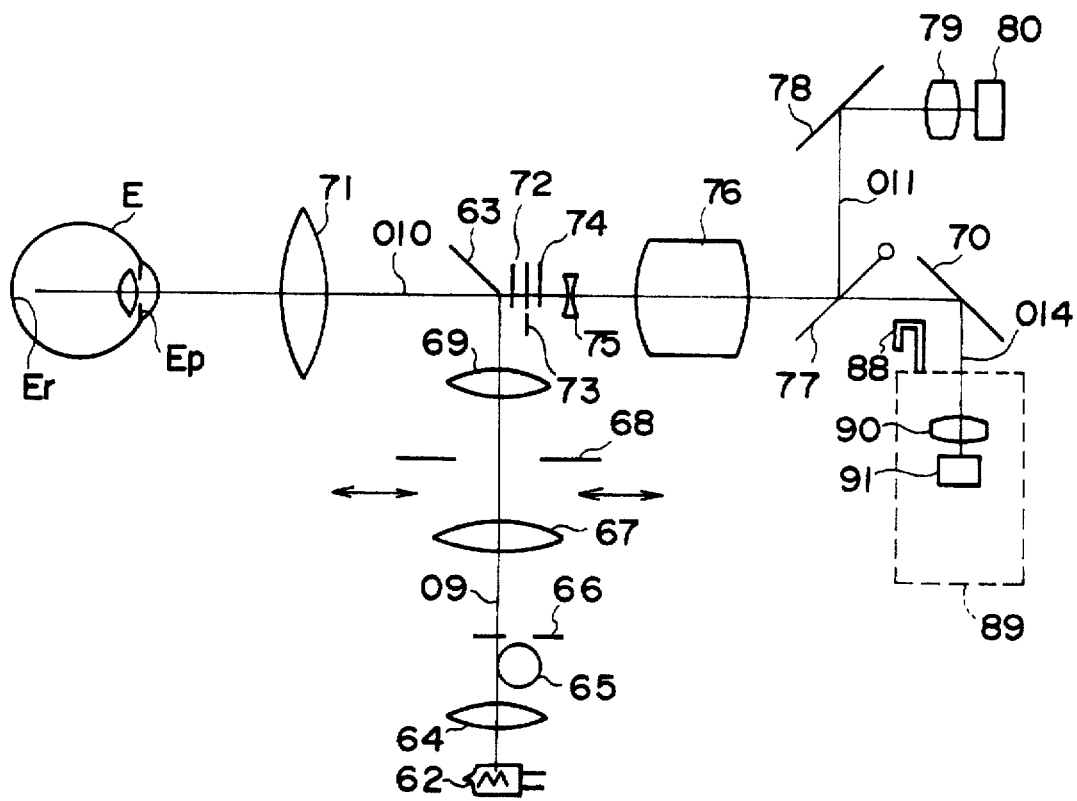
FIG. 23 shows a construction of a fifth embodiment.

FIG. 23 shows a fifth embodiment. Arranged on an optical axis 09 extending from an eye fundus illumination light source 62 to a half-mirror 63 are a condenser lens 64, a stroboscope light source 65, a rectangular diaphragm 66, a relay lens 67, a view field diaphragm 68 and a relay lens 69, and arranged on an optical axis 010 are an objective lens 71, a half-mirror 63, a light shielding member 72 shown in FIG. 24, a photographing diaphragm 73 having two apertures 73a shown in FIG. 25, a light shielding member 74 shown in FIG. 26, a focusing lens 75, a variable magnification lens 76 driven along the optical axis, and a quick-return mirror 77 which retracts from the optical path. An observation optical system shown in FIG. 27 is provided on an optical axis 011 along a reflection direction of the quick-return mirror 77, and a mirror 78, a relay lens 79 and a split prism 80 are provided therein. Arranged on optical axes 012 and 013 split by the split prism 80 are mirrors 81 and 82, poroprisms 83 and 84, and eye pieces 85 and 86, respectively.

Figure 28:
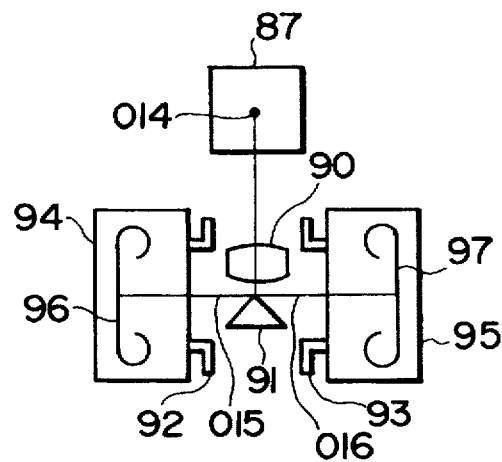
FIG. 28 shows a construction of a photographing optical system.

A photographing optical system shown in FIG. 28 is provided on an optical axis 014 on the opposite side of the mirror 70, and a relay lens 90 and a split prism 91 are arranged in a stereoscopic unit 89 having a mount 88 therein. Arranged on optical axes 015 and 016 split by the split prism 91 are camera packs 94 and 95 having mounts 92 and 93, respectively, and films 96 and 97 are packed therein.

The rectangular apertures 66, the split prisms 80 and 91 and the photographing diaphragm 73 are in conjugate relation with the pupil Ep of the eye E under test, and the view field diaphragm 68 is in conjugate relation with an emmetropic eye fundus Er.

On observing the eye fundus the quick-return mirror 77 is inserted into the optical axis 010 and the light beam from the eye fundus illumination light source 62 passes through the condenser lens 64, the rectangular aperture diaphragm 66, the relay lens 67, the view field diaphragm 68, the relay lens 69, the half-mirror 63 and the objective lens 71 and illuminates the eye fundus Er of the eye E under test. The eye fundus reflected light beam returns on the same optical path, passes through the objective lens 71, the half-mirror 63, the light shielding member 72, the photographing diaphragm 73, the light shielding member 74, the focusing lens 75 and the variable magnification lens 76, is reflected by the quick-return mirror 77 and the mirror 78, passes through the relay lens 79, is split by the split prism 80 to the left and right parts which pass through the mirrors 81 and 82, the poroprisms 83 and 84 and the eye pieces 85 and 86 so that the eye fundus images can be observed by both eyes E of the operator.

On photographing the eye fundus the quick-return mirror 77 is retracted from the optical axis and the stroboscope light source 65 is fired. The light beam from the stroboscope light source 65 passes through the rectangular aperture diaphragm 66, the relay lens 67, the view field diaphragm 68, the relay lens 69, the half-mirror 63 and the objective lens 71 and is projected onto the eye fundus Er. The eye fundus reflected light beam returns along the same optical path, passes through the objective lens 71, the half-mirror 63, the light shielding member 72, the photographing diaphragm 73, the light shielding member 74, the focusing lens 71, the half-mirror 63, the light shielding member 72, the photographing diaphragm 73, the light shielding member 74, the focusing lens 75 and the variable magnification lens 76, is reflected by the mirror 77, passes through the relay lens 90, and is split by the split prism 91 into the left and right parts, which are photographed as the eye fundus images on the films 96 and 97 packed in the camera backs 94 and 95.

Since the light beam in the stereoscopic unit 89 is reflected vertically only once, the inversion of the eye fundus image is cancelled off by the split prism 91 and no inversion of the image occurs.

To vary magnification of photographing, the variable magnification lens 76 is driven along the optical axis. Since the conjugate position with the pupil moves, the split prism 80 and 91 are not in conjugate relation with the pupil in a strict sense but they can be considered to be substantially in the conjugate relation. The view field diaphragm 68 is driven along the arrows in FIG. 23 to limit the illumination light beam M5 in the direction of the plane of the drawing with the variation of the magnification.

In the present embodiment, non-uniformity of the illumination does not occur in the front portion of the eye photographing mode because the ring slit is not used.

In an observation optical system, if the relay lens 79, the split prism 80, the mirrors 81 and 82, and the poroprisms 83 and 84 are detachable, a monocular observation optical system and a binocular observation optical system can be selectively used. Since the inversion of the image of the relay lens 79 in the binocular observation optical system shown in FIG. 27 is corrected by the poroprisms 83 and 84, the image can be observed in the same manner as that viewed in the monocular eye observation optical system.

Since the mounts 92 and 93 of the camera backs 94 and 95 and the mount 88 of the stereoscopic unit 89 are of the same member, the camera backs 94 and 95 may be directly attached to the apparatus for photographing and one of the camera backs 94 and 95 may be replaced by a television camera or an instant camera. In this case, an ND filter may be used for an exposure adjustment.

Figure 29:
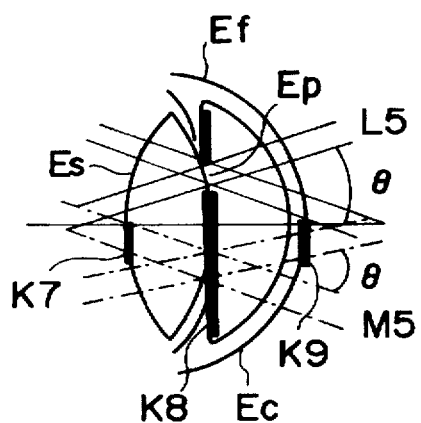
FIG. 29 shows a sectional view of a light beam in a front portion of the eye.
Figure 30:
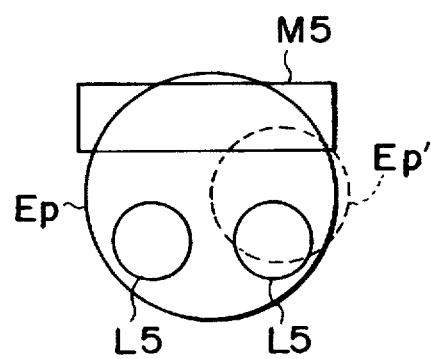
FIG. 30 illustrates a relation between an illumination light beam and a photographing light beam in a pupil.

FIG. 29 shows a sectional view of the light beam in the front portion of the eye Ef. A chain line shows the illumination light beams M5, a solid line shows the photographing light beam L5, and thick solid lines K7–K9 shows the images of the light shielding member 72, the photographing diaphragm 73 and the light shielding member 74, respectively. The image K7 of the light shielding member 72 is located on the rear plane of the crystalline lens Es of an examined eye E. The image K8 of the photographing diaphragm 73 is located at the pupil Ep, and the image of the light shielding member 74 is located at the cornea Ec. The light shielding members 72 and 74 and the photographing diaphragm 73 meet the relations shown in FIGS. 24 to 26 with respect to the optical axis 010. A portion of the oblique light beam of the photographing light beam L5 exiting from the upper portion of the pupil Ep can be partially shielded by the light shielding members 72 and 74. The illumination light beam M15 and the photographing light beam L5 are separated at the front portion of the eye. When the puil Ep is smaller than the two photographing light beams L5 as shown by Ep' as shown in FIG. 30, the stereoscopic photographing can not be attained and normal photographing is conducted by using one photographing light beam L5.

When a strong convex lens of approximately 50 dioptries is inserted in the vicinity of the photographing diaphragm 73, an enlarged stereoscopic photograph of the anterior portion of the eye can be taken.

In a wide angle photographing mode, an angle θ made by the photographing light beam L5 shown in FIG. 29 is large and it is necessary to increase spacings between the shielding member 72, the photographing diaphragm 73 and the shielding member 74, and the illumination light beam. Thus, those members are moved along arrow as shown in FIGS. 24 to 26.

FIG. 31 shows an example of drive means for the light shielding members 72 and 74 and the photographing diaphragm 73. The light shielding members 72 and 74 are integrally assembled by a connecting rod 100, the photographing diaphragm 73 and the light shielding member 74 are coupled to a stepping motor 104 by joints 101 and 102 and a connecting rod 103, and a guide 105 is provided in the photographing diaphragm 73. A ratio of distances from the center 104a of the stepping motor 104 to the joints 101 and 102 is 2 to 1, and a ratio of vertical movements by the rotation of the stepping motor 104 for the photographing diaphragm 73 and the light shielding members 72 and 73 is 2 to 1. The photographing diaphragm 73 is guided by a guide 105 so that it is driven normally to the optical axis 010. Arrows in FIGS. 31 and 24 to 26 show directions of movement of the members when the stepping motor 104 is rotated.

FIG. 32 shows a modification of the observation optical system. A mirror 111, a relay lens 112 and a split prism 113 are arranged on an optical axis 011, and roofprisms 114 and 115 and poroprisms and eye pieces, not shown, similar to those of FIG. 27 are arranged on optical axes 017 and 018. The reflected light beam from the eye fundus Er is reflected by the mirror 111 to the opposite direction to the eye e of the operator, passes through the relay lens 112, is split by the split prism 113, and is reflected again to the eye e of the operator by the roofprisms 114 and 115 so that the vertical inversion is corrected.

In the observation optical system of this embodiment, since the optical axis is folded over, the distance from the eye e of the operator to the examinee can be shortened.

FIG. 33 shows a further modification. The quick-return mirror 77 and the mirror 70 shown in FIG. 23 are integrally assembled and an inversion mirror 120 is provided. The observation optical system shown in FIG. 32 is arranged on the upper optical axis 011 and the photographing optical system shown in FIG. 28 is arranged on the lower optical axis 014 so that the optical systems are reduced in size.

In the observation mode, the inversion mirror 120 is in a solid line position and the eye fundus reflected light beam is reflected 90 degrees upward, passes through the mirror 111, the relay lens 112 and the split prism 113 in the observation optical system shown in FIG. 32, and reaches the eye e of the operator.

In the photographing mode, when the inversion mirror is rotated to a dotted line position, the eye fundus reflected light beam is reflected by the inversion mirror 120 by 90 degrees downward, passes through the relay lens 90 and the split prism 91 of the photographing optical system and reaches the films 96 and 97 as in FIG. 28. Since the camera backs 94 and 95 may be attached downwards, a face of an operator will not hit the camera backs 94 and 95 even if an eye point of a finder is located in a front position.

The optical system of FIG. 33 comprising the mirror 77 and the split prism 80 may be used monocularly. On this occasion, a monocular finder and a single camera body are used.

An eye fundus photographing apparatus described below illuminates an eye fundus of an eye under test through one side of a pupil through an objective lens and photographs it through the other side of the pupil. It has a wide photographing frame horizontally.

In the present eye fundus photographing apparatus, the illumination light beam and the photographing light beam are separated at the pupil and the peripheral light beam in the vertical direction is also separated at the front portion of the eye. Accordingly, the photographing angle in that direction is more widened.

Figure 34:
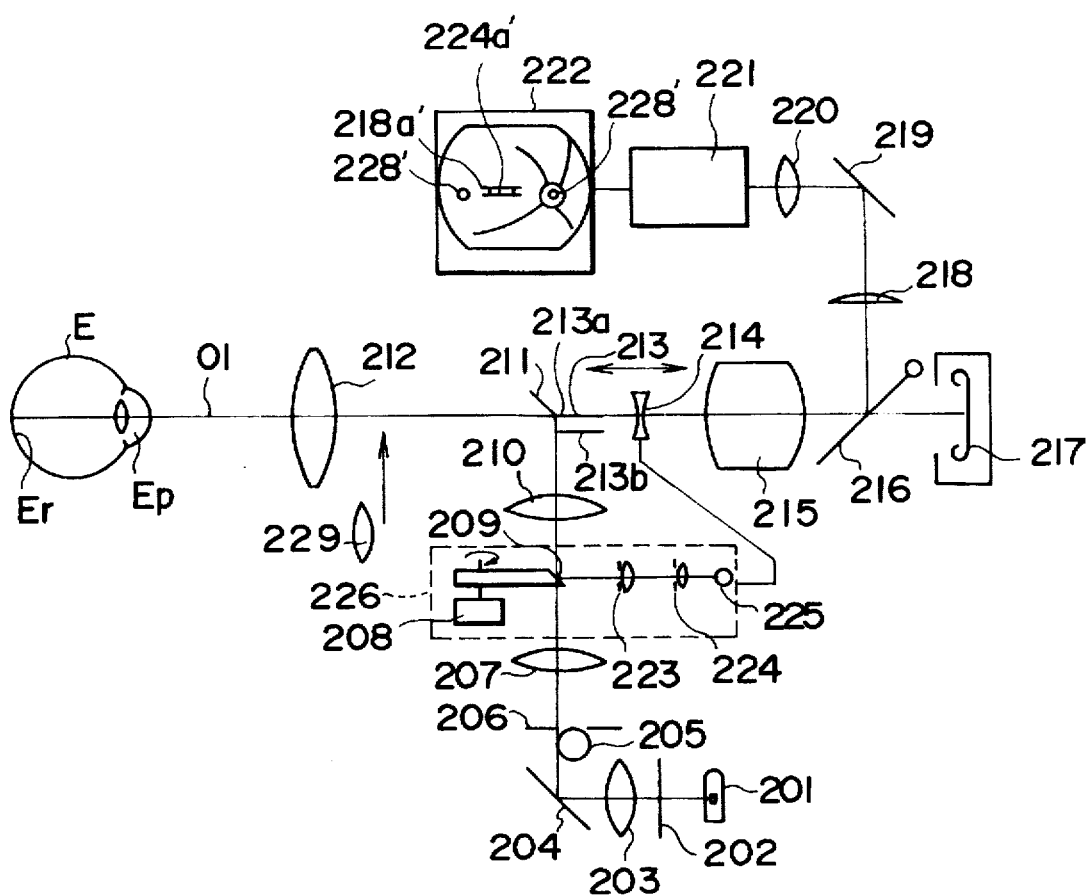
FIG. 34 shows a construction of a sixth embodiment.
Figure 35:
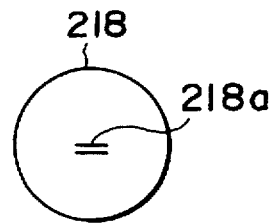
FIG. 35 shows a field lens.

FIG. 34 shows a construction of a non-midriatic eye fundus camera in a sixth embodiment of the present embodiment. Orderly arranged on an optical axis 01 extending from an observation light source 201 to an eye E under test are an infrared filter 202, a condenser lens 203, a mirror 204, a photographing light source 205 such as stroboscope tube, a diaphragm 206 having a crescent-shaped aperture, a relay lens 207, a small mirror retractably driven by drive means 208 and from the optical axis 01, a relay lens 210, a half-mirror 211 arranged on one half side of the optical path and an objective lens 212. Arranged behind the half-mirror 211 are a composite diaphragm 213 including two square light shielding plates 213a and 213c arranged on the other half area to the half-mirror 211 and a circular apertured plate 213b sandwiched between the light shielding plates 213a and 213c, a focusing lens 214, a taking lens 215 a quick-return mirror 216 which may be jumped up, and a photographing film 217. A field lens 218 having two lines 218a drawn thereon, as shown in FIG. 35, a mirror 219, a lens 220 and a television camera 221 are arranged along the direction of reflection by the quick-return mirror 216 and the eye fundus image can be observed by a television monitor 222.

A diaphragm 223 having a semi-circular aperture 223a as shown in FIG. 36A and in substantially conjugate relation with the pupil Ep, a diaphragm 224 having a slit aperture 224a as shown in FIG. 36B and in substantially conjugate relation with the eye fundus Er, a light source 225 and various lenses are arranged along the direction of reflection by the small mirror 209. They form together with drive means 28 and the small mirror 209 a focus detection index projection optical system 226 which is moved along the optical axis 01 with the focusing lens 214.

FIG. 37 shows a front view of the vicinity of the half-mirror 211 as viewed from the eye E under test. A light source 227 arranged on the optical axis to serve as a fixed viewing light in observing the front portion of the eye and a light source 228 for distance setting are provided between the half-mirror 211 and the circular aperture plate 213b. An auxiliary lens 229 is removably mounted behind the objective lens 212 and it is used in observing the front portion of the eye.

In photographing the eye fundus, the auxiliary lens 229 is first inserted into the optical path, and the light source 227 and the light source 228 are lighted and the front portion of the eye is observed by using the television camera 221. Two marks, a crescent-shaped mark and a circular mark are electrically generated by a mark generator, not shown, on the television monitor 222 as shown in FIG. 38 and alignment is employed such that the marks are aligned to coincide with the pupil image Ep' of the eye E under test. When the alignment is to some extent attained, the auxiliary lens 229 is removed from the optical path and the eye fundus image is observed to focus the cornea reflected image 228' of the light source 228. The image 206' of the diaphragm 206 is projected onto the half-mirror 211 as shown in FIG. 37. Since thereby the light beam is projected into the eye from the lower portion of the pupil Ep of the eye E under test, the projection light beam is not often hindered by eyelashes.

Then, the drive means 208 is driven to arrange the small mirror 209 onto the optical axis 01 and the light source 225 is lighted. The light beam emitted from the light source 225 illuminates the eye fundus Er and the eye fundus reflected light beam is sensed by the television camera 221 and displayed on the television monitor 222. The index projection optical system 226 is moved along the optical axis 01 and the focusing lens 214 is moved therewith while keeping the conjugate relation with the photographing film 217.

When the image 218a' of the lines 218a of the field lens 218 aligns to the image 224a' of the slit 224a of the index projection optical system 226 on the television monitor 222 as shown in FIG. 34, the focusing is attained on the photographing film 217.

When the focusing on the photographing film 217 is completed, the small mirror 200 is rotated to retract it from the optical path and the jump-up mirror 216 is jumped up and the photographing light source 206 is lighted to photograph the eye fundus.

FIG. 39 shows a reaction between the light beam in the eye E under test and the diaphragm image. The light beams La, Lb and Lc for illuminating three points A, B and C of the eye fundus Er pass through the aperture of the diaphragm image 206' on the pupil Ep, are incident on the eye E under test, and the eye fundus reflected light beams becomes La', Lb' and Lc' to pass through the image 213' of the composite diaphragm 213 and exit out of the eye E under test. The composite diaphragm image 213' forms three partial images 213a', 213b' and 213c' in the vicinity of the pupil Ep in accordance with the actual construction of the composite diaphragm 213.

FIG. 40 shows a front view of the pupil Ep and FIGS. 41A, 41B and 41C show the sections at the images 213a', 213b' and 213c'. As shown in FIGS. 41A to 41C, the lower portion of La' and the upper portion of Lc' are blocked by images 213a' and 213c' respectively. The incident light to the eye E under test and the eye fundus reflected light beam in the front portion of the eye are separated so that the eye fundus image with a high contrast can be attained. The illumination light beam onto a point D on the eye fundus in FIG. 42 and the reflected photographing light beam spread only horizontally in the front portion of the eye, and even if a view field is widened in this direction, it does not affect against the separation state of the illumination light beam and the reflected photographing light beam which are separated vertically. Accordingly, the image having a wider lateral length can be attained.

The number of the lines 218a of the field lens 218 may be one and the center of the slit image 224a' may be aligned to the single image 218a'. An optical finder may be used. If the television monitor 222 is used to observe, cursor lines can be also electrically generated instead of providing two lines 218a on the field lens 218.

An eye fundus photographing apparatus described below illuminates the eye fundus of the eye under test from one side of the pupil of the eye under test through the objective lens and photographs it from the other side of the pupil of the eye under test. It comprises an index projection optical system and a sensing optical system for sensing the eye fundus reflected light beam through the objective lens. It is characterized by detecting the focusing by the position of the eye fundus reflected light on the observation plane.

The present eye fundus photographing apparatus detects the focusing by the position of the index on the observation plane projected to the eye fundus of the eye fundus test.

FIG. 43 shows a seventh embodiment. It is an automated version of the focusing system of FIG. 34. A diaphragm 242 having a slit aperture and a lens 243 are arranged in front of a focusing light source 241, and a dichroic mirror 244 is arranged at a position corresponding to the mirror 204 of FIG. 34 and it extends to an optical axis 01. A dichroic mirror 245 is arranged immediately behind a composite diaphragm 213 and a lens 246, a cylindrical lens 247 for forming a linear image and a linear array line sensor 248 (such as CCD) are arranged along the direction of reflection, and an image is arranged perpendicularly to the linear array line sensor 248. A computer 249 is connected to the line ar array line sensor 248 and it controls drive means 250 which drives the focusing lens 214 in response to the signal of the linear array line sensor 248. A lens 251 and an observation light source 252 are provided in the direction reflected by the dichroic mirror 244.

In the focusing mode, the light source 241 is lighted and the light beam is projected onto the eye fundus Er. The eye fundus reflected light is reflected by the dichroic mirror 245 behind the composite diaphragm 213, passes through the lens 246 and the cylindrical lens 247 and is focused on the linear array line sensor 248 as shown in FIG. 44. Since the cylindrical lens 247 has a refractive power perpendicularly to the linear array line sensor 248, the image 242' of the diaphragm 242 is an elongated image perpendicular to the linear array line sensor 248. Since the sensing position on the liner array line sensor 248 depends on the viewing angle of the eye E under test, the distance of the drive of the focusing lens is determined by the sensing position of the diaphragm image 242' of the diaphragm 242 so that the focusing can be attained.

Figure 48:
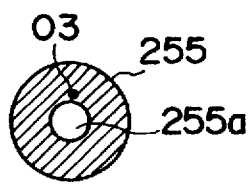
FIG. 48 shows a front view of a photographing diaphragm.
Figure 49:
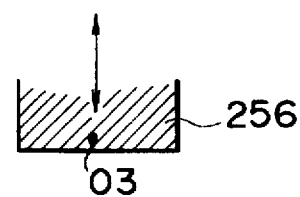
FIG. 49 shows a front view of a light shielding plate in a photographing system.

FIG. 45 shows a portion of a construction of a third embodiment having the variable magnification function. Arranged on an optical axis 02 in front of the photographing light source 205 are an illumination diaphragm 253 having a crescent-shaped aperture 253a which is eccentric to the optical axis 02 as shown in FIG. 46, a relay lens 207, a view field diaphragm 254 including a rectangular aperture 254a and two plates 254b and 254c as shown in FIG. 47 in which the aperture 254a is variable by moving the plates 254b and 254c, a half-mirror 211. Arranged behind the half-mirror 211 in the optical path 03 are a pupil conjugate photographing diaphragm 255 having a circular aperture 255a as shown in FIG. 48, two square light shielding plates 256 provided in front of and behind the diaphragm 255 and movable perpendicularly to the optical axis 03 as shown in FIG. 49 and a photographing lens 257, and a photographing film 217. The illumination diaphragm 253 and the two light shielding plates 256 are movable on the optical axis perpendicularly to the optical axis and they are moved in response to the magnification.

In a wide angle photographing mode, two plates 254b and 254c of the view field diaphragm are opened to expand the field of view. Since the image angle of the photographing light beam increases, the illumination diaphragm and the light shielding plate 256 are moved to increase the separation of the illumination light beam and the photographing light beam on the pupil Ep. The light shielding plate 256 may have a circular aperture diaphragm but because the reduction of light in the periphery occurs, using a one-direction light shielding plate is preferable. It is preferable to use two light shielding plates 256 as in this embodiment. But a certain degree of effect can be attained even when only one is used. It is preferable that the axial position of the view field diaphragm 254 can be adjusted for keeping it in conjugate relation with the eye fundus although it may be fixedly arranged at the conjugate position to the fundus Er of an emmetropic eye as in this embodiment.

Figure 50:
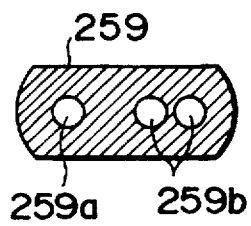
FIG. 50 shows a front view of a stereoscopic diaphragm.
Figure 51:
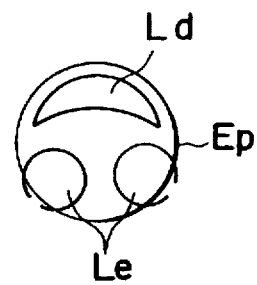
FIG. 51 illustrates a light beam in a stereoscopic photographing.

FIG. 50 shows a front view of a photographing diaphragm 259 in a fifth embodiment which enables the stereoscopic observation and photographing. The photographing diaphragm 259 is used in place of the illumination diaphragm 253 shown in FIG. 45. A monocular unit 259a and a binocular unit 259b are arranged on one same plate, which is slid to switch the monocular eye observation or the binocular observation. FIG. 51 shows a relation of light beams on the pupil Ep in the stereoscopic mode. The illumination light beam Ld and the photographing light beam Le are vertically and horizontally separated, the one-dimensional light shielding plate 256 and the illumination diaphragm 253 of the eighth embodiment may be used as they are, the optical path is laterally split at the pupil conjugate position into left and right path. A binocular observation finder or stereoscopic film camera bodies for forming left and right images are used.

Figure 52:
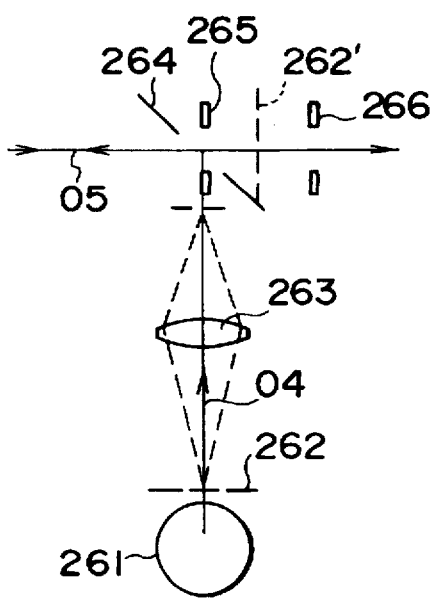
FIG. 52 shows a main construction of a tenth embodiment.

FIG. 52 shows a construction of major parts of the eye fundus photographing apparatus of the tenth embodiment. Arranged on an optical axis 04 in front of a light source 261 are a ring slit 262 having a ring-shaped aperture, a lens 263, and an apertured mirror 264 having an aperture at a center and an eye E under test is located along the direction of reflection of the apertured mirror 264. Arranged on an optical axis 05 in front of the eye E under test are an apertured mirror 264 and two circular diaphragms 265 and 266 (one of which is also used as a photographing diaphragm) having circular apertures at the center and arranged in front of and behind a conjugate image 262' of the ring slit 262, and they apply to the photographing and observation optical systems.

Figure 53:
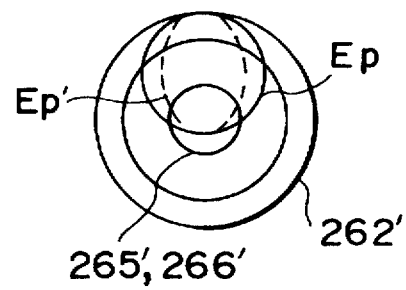
FIG. 53 shows a front view of a pupil.

FIG. 53 illustrates a positional relation between the images projected to the pupil Ep, in which a pupil diameter is small. Since the pupil diameter is smaller than the ring slit image 262', the ring slit image 262' for forming a concentric image and the diaphragm images 265' and 266' are eccentric to the pupil Ep.

Figure 54:
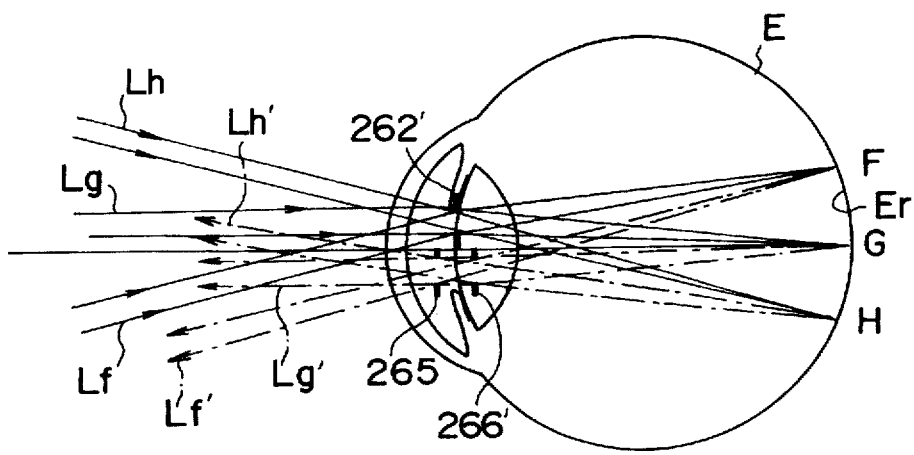
FIG. 54 shows an optical path in an eye.

FIG. 54 shows a longitudinal sectional view of the eye E under test and shows an internal light beam status. The image 262' of the ring slit 262 is formed at the top of the eye E under test and the images 265' and 266' of the circular diaphragms 265 and 266 are arranged at the bottom. The illumination light beams Lf, Lg and Lh for illuminating the points F, G and H under consideration on the eye fundus are partially shielded by those three images 262', 265' and 266' and the illumination light beams Lf, Lg and Lh and the eye fundus reflected light beams Lf', Lg' and Lh' can be completely separated at the front portion of the eye so that no scattering nor flare takes place.

The illumination light beam in FIG. 54 shows a longitudinal sectional light beam. The separation of the illumination light beam and the photographing light beam is substantially the same as that at the center. Since the illumination light beam is shielded only by the ring slit 262, the eye fundus Er is not blocked and it is uniformly illuminated. The light shielding by the circular diaphragms 265 and 266 diameters are preferably 20–30% of the center light beam diameter. The brightness of the center is approximately one half of that of the periphery but the non-uniformity of illumination is not prominent. The non-uniformity of illumination may be auto-exposure controlled by the film plane reflection. If the illumination is uniform, a center weighing photo-metering method may be used to attain more proper exposure.

In photographing the periphery of the eye fundus, the pupil is obliquely observed. An apparent pupil shape is elliptic as shown by Ep' in FIG. 53. In the eccentric illumination, the light intensity and the uniformity are same as these for the center photographing and proper exposure is attained. When a viewing line is swung vertically, the eccentricity is made horizontally.

Figure 55:
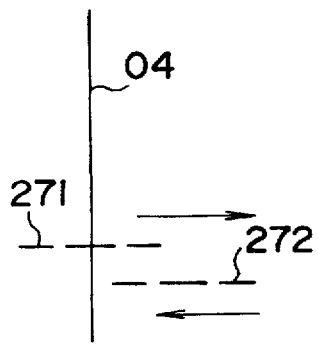
FIG. 55 shows an arrangement of a ring slit.
Figure 56:
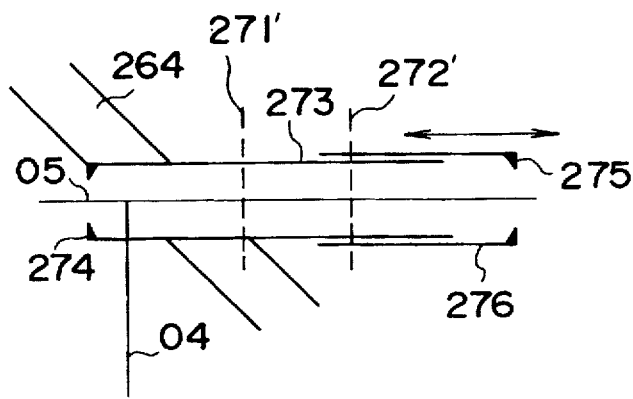
FIG. 56 shows an arrangement of a circular diaphragm.

FIGS. 55 and 56 illustrate the diaphragm of the eye fundus photographing apparatus shown in FIG. 52 having a variable image angle optical system. FIG. 55 shows the vicinity of the ring slit 262 and FIG. 56 shows the vicinity of the apertured mirror 264. A wide angle slits 271 and a narrow angle slit 272 having different sizes from each other are removably arranged at different positions on the optical axis 04. In the wide angle photographing mode, the wide angle slit 271 is inserted, and in the narrow angle photographing mode, the narrow angle slit 272 is inserted. A tube 273 for guiding the light beam is provided in the aperture of the apertured mirror 264 along the optical axis 05, and a circular diaphragm 274 having a circular aperture is provided at an end of the tube 273 facing the eye E under test. A slidable tube 276 which is slidable relative to the tube 273 along the optical axis 05 and has a circular diaphragm 275 at an end facing the photo-detector is provided. The spacing of the circular diaphragm 275 to the circular diaphragm 274 is variable.

In the wide angle photographing mode, the wide angle slit 271 is inserted onto the optical axis 04, the slidable tube 276 is pushed into the apertured mirror 264, and the spacing between the circular diaphragms 274 and 275 is reduced. By reducing the spacing 275 of the circular diaphragm, the vignette is prevented even if the image angle is selected wide. In the narrow angle photographing mode, the wide angle slit 271 is exchanged with the narrow angle slit 272, and the slidable tube 276 is pulled out to increase the spacing between the circular diaphragms 275 and 274.

When the pupil diameter is large, the illumination may be made while the pupil Ep and the ring slit 262 are kept concentric as it is in the prior art apparatus. The circular diaphragm 275 may not be of the slide type but a narrow angle one and a wide angle one may be separately provided and may be alternatively inserted into the optical axis in accordance with a purpose of photographing. In order to separate the optical path, it is more preferable that a variable view field diaphragm may be provided in the illumination optical system to vary it in accordance with the change of the image angle.

Figure 57:
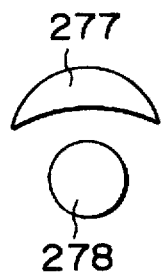
FIG. 57 shows an arrangement of a light beam on a pupil in a non-scattering pupil eye fundus camera.

FIG. 57 illustrates a relation of light beams on the pupil of the non-midriatic eye fundus camera. An illumination diaphragm, not shown, is of crescent shape, and a crescent-shape diaphragm image 277 and a photographing light beam image 278 are arranged on the pupil Ep. In order to photograph only a central portion of the fundus, the illumination light beam may be fixed in a predetermined direction.

Though a fundus camera has been explained as above the present invention may be applied to an ophthalmoscope for observing fundus. In this case, the objective lens may be separated like a conventional indirect opthalmoscope and it may be used as a hand-held.

In accordance with the eye fundus photographing apparatus of the present invention, even if the pupil diameter is small, the observation photographing is attained because the eye fundus illumination light beam and the photographing light beam are separated at the front portion of the eye.

What is claimed is:

1. An eye fundus imaging apparatus comprising:
    an illumination system for illuminating an eye fundus of an eye being examined using an illumination light beam, said illumination system having an illumination diaphragm at a position substantially conjugate to a pupil of the eye and having at least one aperture at a position corresponding to at least one area of the eye pupil;
    an imaging system for imaging the eye fundus using an imaging light beam from the eye fundus illuminated by said illumination system, said imaging system having an imaging diaphragm at a position substantially conjugate to the eye pupil and said imaging diaphragm having at least one aperture at a position corresponding to at least one different area of the eye pupil than the at least one area, the at least one area and the at least one different area being arranged so that the at least one area and the at least one different area are spaced from each other in one direction, wherein one of two perpendicular axes passes through both the at least one area and the at least one different area and the other of the two perpendicular axes passes through only one of the at least one area and the at least one different area; and
    at least one light shielding member arranged at one of (i) a vicinity of one of said illumination diaphragm and said imaging diaphragm and (ii) a vicinity of a conjugate position of one of said illumination diaphragm and said imaging diaphragm, said at least one light shielding member being provided at a position to separate the illumination light beam and the imaging light beam at a front portion of the eye.

2. An eye fundus imaging apparatus according to claim 1 wherein said light shielding member is provided on both sides of an optical axis of the illumination diaphragm, and each portion of the light shielding member partially and equally shields the light beam passing along the optical axis in the front portion of the eye to separate the illumination light beam and the imaging light beam in the front portion of the eye.

3. An eye fundus imaging apparatus according to claim 1 further comprising a cylindrical lens provided at one of a vicinity of said imaging diaphragm and at a vicinity of a conjugate position of said imaging diaphragm.

4. An eye fundus photographing apparatus according to claim 1 wherein said imaging system further comprises a split reflecting member arranged at one of a position conjugate to the eye pupil and a position at a vicinity of the eye pupil, and imaging units arranged in optical paths split by said split reflecting member.

5. An eye fundus imaging apparatus according to claim 1 further comprising an observation system having an optical system partially shared by said imaging system for observing an eye fundus image, and a reflection member for reflecting the light beam from the eye to an observation system and being rotated by 90 degrees at the time of imaging to direct the light beam from the eye to said imaging system by reflection.

6. An eye fundus imaging apparatus according to claim 1 wherein said light shielding member is provided at a vicinity of said imaging diaphragm and said imaging diaphragm means is moved with said light shielding member in varying a magnification of said imaging system.

7. An eye fundus imaging apparatus according to claim 1 further comprising optical path selecting means for selecting the optical path from said imaging system, a split reflecting member arranged at a position conjugate to the pupil in the optical path selected by said optical path selecting means and means for directing the optical paths split by said split reflecting member to left and right eyes of an examined person.

8. An eye fundus imaging apparatus according to claim 1 further comprising a long photograph screen perpendicular to the separating direction of the imaging light beam reflected by the eye from the illumination light beam propagating to the eye fundus at the pupil.

9. An eye fundus imaging apparatus according to claim 1 further comprising an index projection system for projecting an index to the eye fundus and an optical system for receiving light reflected from the eye fundus to a plane through said imaging diaphragm, wherein the focusing of said imaging system is detected based on a position of the received light.

10. An eye fundus imaging apparatus according to claim 1 wherein said light shielding member shields a light beam along the illumination light beam at a vicinity of said imaging diaphragm.

11. An eye fundus imaging apparatus according to claim 1 wherein said illumination diaphragm has a ring-shaped aperture arranged such that the image partially overlays the pupil when the pupil is small.

12. An eye fundus imaging apparatus according to claim 1 wherein said illumination diaphragm has a crescent-shaped aperture.

13. An eye fundus imaging apparatus according to claim 1 wherein said illumination diaphragm and said imaging diaphragm are variable in accordance with a photographing image angle of said imaging system.

14. An eye fundus imaging apparatus according to claim 1 wherein said light shielding member and said illumination diaphragm are composed of two diaphragms.

15. An eye examining apparatus comprising:
an illumination system for illuminating an eye fundus of an eye being examined using an illumination light beam, said illumination system having an illumination diaphragm at a substantially conjugate position to a pupil of the eye and having at least one aperture at a position corresponding to at least one area of the eye pupil;
an imaging system for imaging the eye fundus using an imaging light beam from the eye fundus illuminated by said illumination system, said imaging system having an imaging diaphragm at a position substantially conjugate to the pupil and having at least one aperture at a position corresponding to at least one different area of the eye pupil than the at least one area, the at least one area and the at least one different area being arranged so that the at least one area and the at least one different area are spaced from each other in one direction, wherein one of two perpendicular axes passes through both the at least one area and the at least one different area and the other of the two perpendicular axes passes through only one of the at least one area and the at least one different area; and
at least one light shielding member arranged at one of (i) a vicinity of one of said illumination diaphragm and said imaging diaphragm and (ii) a vicinity of a conjugate position of one of said illumination diaphragm and said imaging diaphragm, said at least one light shielding member being provided at a position to separate the illumination light beam and the imaging light beam at a front portion of the eye.

16. An eye examining apparatus comprising:
an illumination system for illuminating an eye fundus of an eye being examined using an illumination light beam, said illumination system illuminating the eye fundus via at least one area of a pupil of the eye;
an imaging system for imaging the eye fundus using an imaging light beam from the eye fundus illuminated by said illuminating system, said imaging system having an imaging diaphragm at a position substantially conjugate to the eye pupil and having at least one aperture at a position corresponding to at least one different area of the eye pupil from the at least one area, the at least one area and the at least one different area being arranged so that the at least one area and the at least one different area are spaced from each other in one direction, wherein one of two perpendicular axes passes through both the at least one area and the at least one different area and the other of the two perpendicular axes passes through only one of the at least one area and the at least one different area; and at least one light shielding member arranged at one of (i) a vicinity of one of said illumination diaphragm and said imaging diaphragm and (ii) a vicinity of a conjugate position of one of said illumination diaphragm and said imaging diaphragm, said at least one light shielding member being provided at a position to separate the illumination light beam and the imaging light beam at a front portion of the eye.

17. An apparatus according to claim 16, wherein said light shielding member includes a linear edge disposed in a imaging optical path.

18. An apparatus according to claim 16, wherein said light shielding member is provided at both sides of an optical axis of said imaging diaphragm.

19. An eye fundus imaging apparatus comprising:
an illumination system for illuminating an eye fundus of an eye being examined using an illumination diaphragm at a position substantially conjugate to a pupil of the eye, wherein the illumination diaphragm has at least one aperture at a position corresponding to one area of the eye pupil;
an imaging system for imaging the eye fundus using an imaging light beam from the eye fundus illuminated by said illumination system, said imaging system having an imaging diaphragm at a position substantially conjugate to the eye pupil, wherein said imaging diaphragm has at least one aperture at a position corresponding to at least one different area of the eye pupil than the at least one area, the at least one area and the at least one different area being arranged on a plane including the pupil of the eye; and
a focus detection system for detecting a focus condition of said imaging system using detection light for detecting the focus condition, wherein the detection light is projected to the eye fundus through an area substantially conjugate to the eye pupil in said illumination system corresponding to a first area including the at least one area wherein the detection light is received from the eye fundus through an area substantially conjugate to the eye pupil in said imaging system corresponding to a second area differing from the first area and including the at least one different area.

20. An eye fundus imaging apparatus comprising:
an illumination system for illuminating an eye fundus of an eye being examining using an illumination diaphragm at a position substantially conjugate to a pupil of the eye, wherein the illumination diaphragm has at least one aperture at a position corresponding to at least one area of the eye pupil; and
an imaging system for imaging the eye fundus using an imaging light beam from the eye fundus illuminated by said illumination system, said imaging system having an imaging diaphragm at a position substantially conjugate to the eye pupil, wherein said imaging diaphragm has at least one aperture at a position corresponding to at least one different area of the eye pupil than the at least one area, the at least one area and the at least one different area being arranged on a plane including the pupil of the eye, said imaging system having an imaging area on the eye fundus wider in a direction perpendicular to an axis passing through the at least one area and the at least one different area than in the direction of the axis passing through the at least one area and the at least different area.

21. An eye fundus imaging apparatus comprising:
an illuminating system for illuminating an eye fundus of an eye being examined;

an imaging system for imaging the eye fundus illuminated by said illuminating system;

imaging displaying means for displaying an image of the eye fundus obtained by said imaging system; and a focus system for focusing the image of the eye fundus, said focus system projecting a light flux on the eye fundus to form an image of the light flux projected on the eye fundus on said image displaying means, and indicating a focus mark, other than a mark formed on the eye fundus, on said image displaying means, the focus mark being usable for focusing of the image of the eye fundus by performing a comparison using the image of the light flux.

22. An eye fundus imaging apparatus comprising:

an illuminating system for illuminating an eye fundus of an eye being examined;

an electrical imaging system for imaging the eye fundus illuminated by said illuminating system;

image displaying means for displaying an image of the eye fundus obtained by said electrical imaging system; and a focus system for focusing the image of the eye fundus, said focus system indicating an electrically-generated focus mark on said image displaying means for being used for focusing of the image of the eye fundus.

* * * * *

UNITED STATES PATENT AND TRADEMARK OFFICE
CERTIFICATE OF CORRECTION

PATENT NO. : 5,713,047  Page 1 of 2

DATED : January 27, 1998

INVENTOR(S) : YOSHIMI KOHAYAKAWA

It is certified that error appears in the above-identified patent and that said Letters Patent is hereby corrected as shown below:

ON THE COVER PAGE

At [56], U.S. Patent Documents

"4,838,680 6/1989 Nowokawa" should read --4,838,680 6/1989 Nunokawa--.

COLUMN 5

Line 52, "ununiformity" should read --non-uniformity--.

COLUMN 7

Line 50, "lelly" should read --lell--.

COLUMN 9

Line 44, "puil" should read --pupil--.

UNITED STATES PATENT AND TRADEMARK OFFICE
CERTIFICATE OF CORRECTION

PATENT NO. : 5,713,047

DATED : January 27, 1998

INVENTOR(S) : YOSHIMI KOHAYAKAWA

It is certified that error appears in the above-identified patent and that said Letters Patent is hereby corrected as shown below:

COLUMN 15

Line 15, "hand-held." should read --hand-held device--.

COLUMN 17

Line 12, photographing" should read --imaging--.

Signed and Sealed this

Twenty-eighth Day of July, 1998

Attest:

BRUCE LEHMAN

Attesting Officer        Commissioner of Patents and Trademarks